US009702795B2

(12) United States Patent
Carragher et al.

(10) Patent No.: US 9,702,795 B2
(45) Date of Patent: Jul. 11, 2017

(54) APPARATUS AND METHOD FOR PRODUCING SPECIMENS FOR ELECTRON MICROSCOPY

(71) Applicants: THE SCRIPPS RESEARCH INSTITUTE, La Jolla, CA (US); ENGINEERING ARTS LLC, Phoenix, AZ (US); Bridget Carragher, San Diego, CA (US); Clinton S. Potter, San Diego, CA (US); Tilak Jain, Encinitas, CA (US); Peter Kahn, Phoenix, AZ (US); Peter Wiktor, Phoenix, AZ (US)

(72) Inventors: Bridget Carragher, San Diego, CA (US); Clinton S. Potter, San Diego, CA (US); Tilak Jain, Encinitas, CA (US); Peter Kahn, Phoenix, AZ (US); Peter Wiktor, Phoenix, AZ (US)

(73) Assignee: The Scripps Research Institute, La Jolla, CA (US)

( * ) Notice: Subject to any disclaimer, the term of this patent is extended or adjusted under 35 U.S.C. 154(b) by 419 days.

(21) Appl. No.: 14/372,277

(22) PCT Filed: Jan. 14, 2013

(86) PCT No.: PCT/US2013/000019
§ 371 (c)(1),
(2) Date: Jul. 15, 2014

(87) PCT Pub. No.: WO2013/109406
PCT Pub. Date: Jul. 25, 2013

(65) Prior Publication Data
US 2014/0360286 A1 Dec. 11, 2014

Related U.S. Application Data

(60) Provisional application No. 61/632,047, filed on Jan. 17, 2012.

(51) Int. Cl.
*G01N 1/28* (2006.01)
*G01N 1/42* (2006.01)
*H01J 37/26* (2006.01)

(52) U.S. Cl.
CPC .............. *G01N 1/28* (2013.01); *G01N 1/2813* (2013.01); *G01N 1/42* (2013.01); *H01J 37/261* (2013.01);
(Continued)

(58) Field of Classification Search
CPC .......... G01N 1/28; G01N 1/2813; G01N 1/42; H01J 37/261; H01J 2237/2001; H01J 2237/2802; H01J 37/26
(Continued)

(56) References Cited

U.S. PATENT DOCUMENTS 3,768,914 A * 10/1973 Kinney .................... G01N 1/31
356/244
6,063,339 A * 5/2000 Tisone ................. B01J 19/0046
422/509

(Continued)

FOREIGN PATENT DOCUMENTS

EP          1995584 A2    11/2008
EP          2381236 A1    10/2011
JP        2000195455       7/2000

OTHER PUBLICATIONS

Barbulovic-Nad, et al., "Bio-Microarray Fabrication Techniques—A Review", *Critical Reviews in Biotechnology* 26: 237-259.
(Continued)

*Primary Examiner* — Wyatt Stoffa
(74) *Attorney, Agent, or Firm* — Hugh Wang; Thomas Fitting

(57) ABSTRACT

The invention provides methods and devices for preparing frozen vitrified samples for transmission electron micros-
(Continued)

Figure 1:
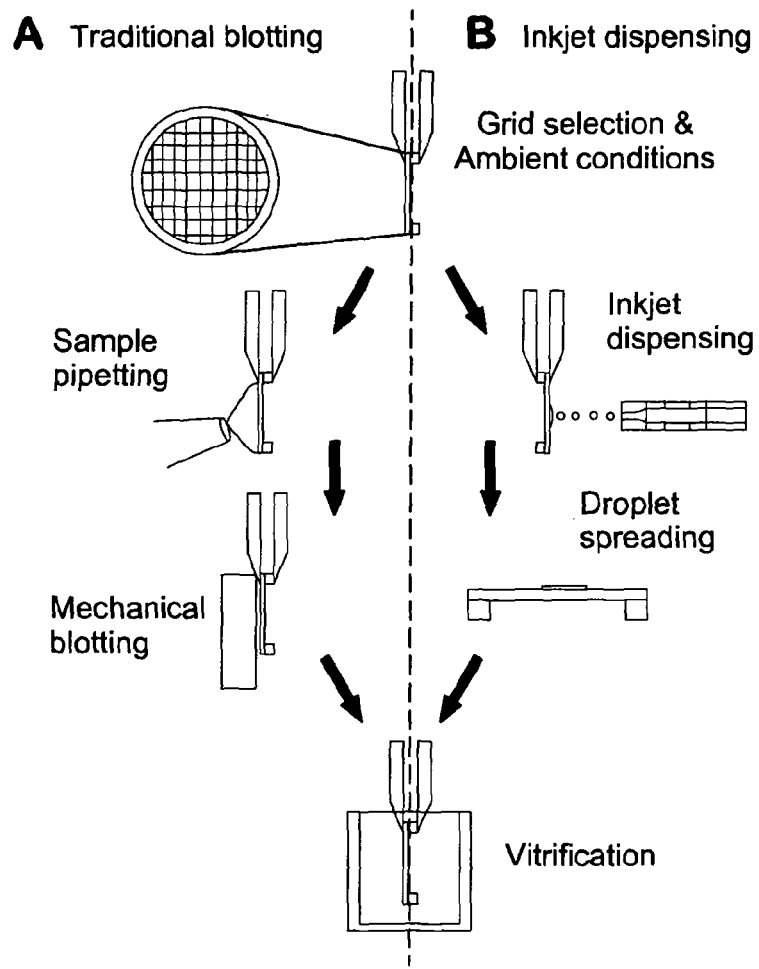
Figure 1:
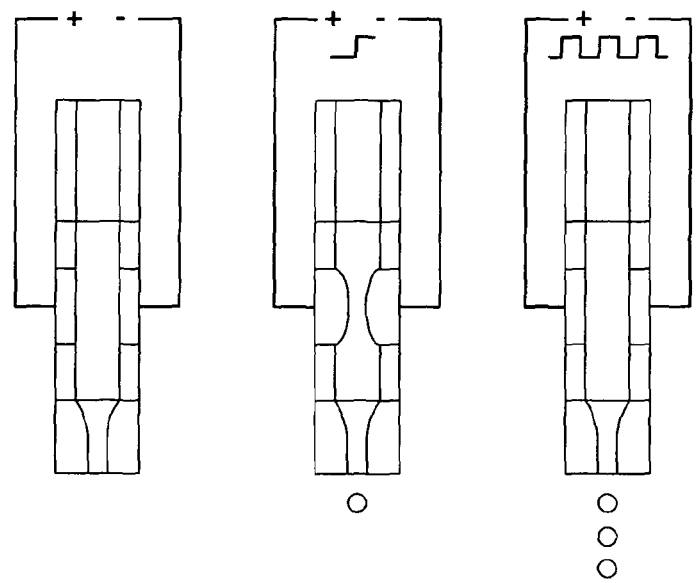

copy. By reducing the volume of sample from microliter scale to picoliter scale, the requirement for blotting of excess fluid is minimized or eliminated.

19 Claims, 7 Drawing Sheets

(52) U.S. Cl.
CPC ....... *H01J 37/26* (2013.01); *H01J 2237/2001* (2013.01); *H01J 2237/2802* (2013.01)

(58) Field of Classification Search
USPC .................................................... 73/863.11
See application file for complete search history.

(56) References Cited

U.S. PATENT DOCUMENTS

| | | | | |
|---|---|---|---|---|
| 6,710,335 B2* | 3/2004 | Ellson | ................ | H01J 49/0454 250/288 |
| 7,754,439 B2* | 7/2010 | Moore | ................ | B01J 19/0046 435/287.1 |
| 2005/0107917 A1* | 5/2005 | Smith | ................ | B25J 15/0253 700/245 |
| 2005/0232823 A1* | 10/2005 | Brock | ................ | B01L 3/0268 73/863.23 |
| 2010/0086573 A1* | 4/2010 | Anderson | ................ | A61K 8/14 424/401 |
| 2010/0112658 A1* | 5/2010 | Hughes | ................ | C12N 1/18 435/161 |
| 2010/0172831 A1* | 7/2010 | Mason | ................ | A61K 9/5184 424/1.29 |
| 2010/0181495 A1* | 7/2010 | Lihl | ................ | G01N 1/42 250/442.11 |
| 2010/0240870 A1* | 9/2010 | Su | ................ | G01N 21/658 530/363 |
| 2011/0192987 A1* | 8/2011 | Qian | ................ | G21K 1/025 250/440.11 |
| 2011/0238225 A1 | 9/2011 | Tripathi et al. | | |
| 2011/0313113 A1* | 12/2011 | Sakamoto | ................ | C08F 2/10 525/384 |
| 2012/0241607 A1* | 9/2012 | Bose | ................ | H01J 37/20 250/307 |
| 2013/0337066 A1* | 12/2013 | Zhang | ................ | A61K 39/0011 424/489 |

OTHER PUBLICATIONS

Berriman, et al., "Analysis of transient structures by cryo-microscopy combined with rapid mixing of spray droplets"; *Ultramicroscopy* 56 (4): 241-252 (1994).

Booth et al., "Visualizing Proteins and Macromolecular Complexes by Negative Stain EM: from Grid Preparation to Image Acquisition", *Journal of Visualized Experiments* 58: e3227 (2011).

https://www.tedpella.com/grids, Gilder Grids.

* cited by examiner

APPARATUS AND METHOD FOR PRODUCING SPECIMENS FOR ELECTRON MICROSCOPY

BACKGROUND OF THE INVENTION

The following discussion of the background of the invention is merely provided to aid the reader in understanding the invention and is not admitted to describe or constitute prior art to the present invention.

Molecular microscopy is a non-invasive electron imaging technology that uses advanced specimen preparation and imaging methods designed specifically to visualize complex biological samples, under conditions close to their native state. Samples are preserved in a very thin film of solution on an EM grid by vitrification (using an automated cryogenic robot) or by negative stain, and then imaged using a transmission electron microscope (TEM) controlled by automated software that enables sampling of a significant portion of the specimen. High-throughput molecular microscopy combines robotic instruments, automated data collection and processing software, and a relational database into a pipeline to prepare, image, and analyze samples in a reproducible manner and with throughputs capable of addressing biopharmaceutical characterization needs in a statistically significant manner. For well-ordered samples such as viruses, and virus-antibody complexes, the achievable resolution can be <0.4 nm.

In preparing EM grids for molecular microscopy, preparation of the sample grid is often the least controlled step in the process. Typically, a few microliters of sample are applied to a specimen grid. Excess sample is removed by contact blotting with a piece of absorbent paper to thin the film of solution. Finally, vitrification, achieved by plunging the thin sample into a liquid coolant (typically liquid ethane). The ultimate thickness of the sample is related to, among other things, the relative hydrophilicity of the grid surface, the relative humidity and temperature of the environment, and the length of blotting time. In addition, once the solution is applied to the grid it has an extremely high surface to volume ratio and its behavior is dominated by the heat and mass transfer that result from evaporation of the aqueous sample. The result of combining these events is that grid surfaces are not reproducible, either within the same grid or within grids. Portions of the specimen grid will be too thick for effective penetration by the electron beam, while others will be too thin for proper specimen preservation, while still others will suffer from increases in solute concentrations due to evaporation of water.

Previously described vitrification robots comprise a guillotine-like grid plunger. The vertical motion is provided by a driven rod to which standard forceps clamping an EM grid are attached. The blotting action is provided by blotting paper attached to rotating disks that are arranged to close on the sample like "clapping hands." The disks rotate to provide a fresh blotting surface for each clap and the duration and pressure of each action are precisely controlled. The entire apparatus is enclosed in an environmental chamber. A shutter at the bottom of the chamber provides access to the rod to load new forceps/grids and to plunge the sample into the coolant. The operational sequence begins with lowering the rod under stepper motor control and attaching the forceps and grid through the opened shutter. The rod retracts and the shutter closes. The sample solution is loaded onto the grid through a hole in the chamber using a pipette to extract solution from a vial inside the chamber, and deposit a controlled amount (typically 3 μL) on the grid. The grid is positioned for blotting and a controlled sequence of blotting actions is performed. The grid is allowed to drain/thin for a controlled period. Finally, the rod is disengaged from the stepper motor and pneumatically propelled (approx. 2 m/sec) through the shutter into the coolant. After vitrification, the coolant reservoir engages the rod/forceps/sample assembly and can be removed from the system to permit further manipulation and transfer to the TEM using conventional cryotransfer tools. All aspects of the preparation sequence are controlled by a computer system that includes an easy-to-use operator interface. See, e.g., Iancu et al., Nat. Protocols 1: 2813-2819, 2007.

Although improving the sample preparation through automating the steps into a more reproducible form, previously described vitrification robots still do not provide the level of sample control necessary for truly reproducible molecular microscopy.

BRIEF SUMMARY OF THE INVENTION

It is an object of the invention to provide methods and devices for preparing frozen vitrified samples for transmission electron microscopy. By reducing the volume of sample from microliter scale to picoliter scale, the requirement for blotting of excess fluid may be minimized or eliminated. In addition, because picoliter scale volumes will not cover an entire EM sample grid surface under achievable contact angles, each EM sample grid may be processed to provide an array of specimen locations on a single grid, each specimen location having relatively reproducible characteristics of sample thickness. This will permit more thorough sampling of each EM grid. Finally, starting volumes may be reduced by a factor of over 1000, which can permit an improved analysis of very precious biological samples.

In a first aspect, the present invention provides a system for preparing an electron microscopy sample on an EM sample grid. The system comprises:

a. a plunger assembly comprising a shaft operably connected to a shaft drive assembly, a triggering mechanism, and a holder for reversibly receiving an EM sample grid at a first end of the shaft, the shaft drive assembly and triggering mechanism configured to (i) position the EM sample grid at a first position prior to a trigger event, and (ii) displace the shaft in a first direction at a predetermined rate and position the EM sample grid at a second position following a trigger event;

b. a drop dispenser configured to dispense fluid from one or more dispensing elements onto one or more independently addressable subregions of the EM sample grid in the first position;

c. a sample reservoir operably linked to the drop dispenser; and d. a cryogen reservoir configured to position a cryogenic liquid at the second position.

In various embodiments, the drop dispenser is configured and arranged to reproducibly dispense volumes smaller than microliter volumes. Preferred drop dispensers dispense in nanoliter volumes, and more preferably picoliter volumes. As used herein, the term "picoliter volumes" refers to a volume of liquid that is at least 1 pL and which is less than 1 nL; "nanoliter volumes" refers to a volume of liquid that is at least 1 nL and which is less than 1 μL; and "microliter volumes" refers to a volume of liquid that is at least 1 μL and which is less than 1 mL.

In alternatives to step b, the drop dispenser may be configured to dispense fluid from one or more dispensing elements onto one or more independently addressable subregions of the EM sample grid between the first position and the second position. This dispensing may occur, for example, in "mid-flight" of the plunger assembly; alternatively, the plunger assembly may be stopped at an intermediate position between the first and second positions.

In various embodiments, the sample volume(s) are applied to subregions of the EM sample grid surface by spotting such as by the use of robotic micropipetting techniques, or more preferably using "ink jet" printing technologies. Ink jet printing technologies known in the art include devices equipped with pins, or sample ejection elements that dispense using thermal, sonic, or piezoelectric impulses. Among the methods mentioned above, the inkjet method is a preferred sample application method because of its ability to carry out high-density, precise spotting.

The inkjet method is a method in which a sample solution of interest is placed in an extra-fine nozzle, pressure or heat is instantaneously applied on a portion near the nozzle's tip to correctly eject an extremely low volume of sample from the nozzle's tip and directed to the surface of the EM grid. For example, the inkjet head may be a bubble-jet head having a mechanism for discharging a solvent with the application of thermal energy; a piezo-jet head that ejects a solution using a piezoelectric element; etc. Preferably, the drop dispenser comprises multiple nozzles that can be used to "print" sample volumes onto discretely addressable locations of the EM sample grid. When the sample solution is ejected from the inkjet head, each sample droplet forms a circular spot, the thickness and expansion of which is controlled by the hydrophilicity of the EM grid surface. Connection with an adjacent spot can be effectively prevented even when the spots of sample solution are spotted in high density.

In certain embodiments, the drop dispenser may be operably connected to a positioning drive configured to provide adjustment of the drop dispenser relative to the EM sample grid in the first position. Preferably, the positioning drive permits mobility in all three axes. Alternatively, the drop dispenser may be held fixed, and the plunger assembly may be operably connected to a positioning drive configured to provide adjustment of the drop dispenser relative to the EM sample grid; or both the drop dispenser and the plunger assembly may be operably connected to positioning drives. Through the use of any of these configurations, the system can flexibly allow for precise location of each dispensing element relative to the grid surface.

As noted above, once the sample solution is applied to the grid it has an extremely high surface to volume ratio and its behavior is dominated by the heat and mass transfer that result from evaporation of the aqueous sample. In order to more rapidly reach an optimal equilibrium between evaporation and condensation at the EM grid surface, an environmental chamber configured to provide controlled relative humidity and temperature may be provided. At its simplest, a transparent box may be placed over the entire apparatus and the interior maintained at a predetermined temperature and humidity. Other configurations will be apparent to one of skill in the art.

In certain embodiments, the system may further comprise one or more of: a first camera system configured to provide monitoring of fluid dispensed from the one or more dispensing elements, and a second camera system configured to provide monitoring alignment of the position of the dispensing elements relative to the EM sample grid in the first position. In certain embodiments this second camera is also used to monitor droplet profiles on the EM sample grid surface.

The plunger shaft may be driven between an "up" (sample application) position and a "down" (sample vitrification) position using a variety of conventional drive mechanisms, such as pneumatic, hydraulic, and electric motor actuators. Alternatively, the drive mechanism may be omitted and the plunger shaft driven downward by gravity. The triggering mechanism is any switch that causes the plunger shaft to move from an up to a down position, and a "triggering event" is an event that initiates this movement. In certain embodiments, the triggering mechanism can act as a toggle, moving the plunger shaft in both directions.

In related aspects, the present invention relates to methods for preparing an electron microscopy sample on an EM sample grid using the system described herein. These methods generally comprise:

a. positioning the EM sample grid on a plunger assembly, the plunger assembly comprising a shaft operably connected to a shaft drive assembly, a triggering mechanism, and a holder for reversibly receiving the EM sample grid at a first end of the shaft, the shaft drive assembly and triggering mechanism configured to (i) position the EM sample grid at a first position prior to a trigger event, and (ii) displace the shaft in a first direction at a predetermined rate and position the EM sample grid at a second position following a trigger event;
b. with the EM sample grid in the first position or between the first and second positions, dispensing one or more sample volumes onto one or more independently addressable subregions of the EM sample grid using a drop dispenser configured to dispense fluid from one or more dispensing elements;
c. activating the triggering mechanism to displace the shaft to the second position, wherein the EM sample grid is immersed into a cryogenic liquid contained within a cryogen reservoir.

The methods of the present invention may be used to prepare frozen vitrified biological samples for detailed analysis by transmission electron microscopy. Suitable biological samples can comprise proteins, viruses, virus-like particles, organelles, liposomes, etc. In view of the interest of regulatory agencies in obtaining information on the aggregation of such therapeutic proteins, preferred specimens are proteins of pharmaceutical interest, such as therapeutic antibodies.

DETAILED DESCRIPTION OF THE INVENTION

Over thirty years ago, Dubochet and colleagues first demonstrated that biological specimens in their native hydrated state could be embedded in vitrified buffer and imaged in the transmission electron microscope (TEM) without loss of structural preservation. This paved the way for the development of cryo-TEM as a field, and the technique has been used to study a vast array of structures over the past 3 decades. Specimens for cryo-EM are normally prepared by embedding them in a thin layer of vitrified ice suspended over an EM grid substrate that may be either continuous or fenestrated. Ideally the vitrified layer should be just slightly thicker than the diameter of the particle (50-500 nm), providing a well distributed and well separated single layer of particles in random orientations.

Current methods of preparing the vitrified sample typically start with applying a relatively large volume (~3 µl) of sample to the surface of an EM grid, then reducing the sample to a thin layer by applying filter paper to one or both sides of the grid to blot away most of the volume, followed by quick plunging into liquid ethane. FIG. 1A. A variety of devices have been developed to try to optimize this method, including both home-made guillotine plungers and more automated commercial devices. All of these devices, however, rely on using macroscopically large filter paper surfaces to try to produce a layer of liquid some 100's of nm thick. These methods allow very limited control of the sample layer on the substrate surface and, not surprisingly, the outcome of these methods is not optimal, normally resulting in large areas of the grid surface area that have vitrified ice that is either too thick or too thin and particles are also sometimes distributed unevenly as a result of varying ice thickness. In addition to the traditional method of specimen pipetting and blotting, variant methods have been described that involve creating a dense spray of specimen (1-20 um droplets) using nebulizers, micro-nozzles and electrospray mechanisms, where the grid is plunged through the sprayed region on its way to vitrification. Droplets landing on the grid surface do not need further blotting and spread out on contact due to surface hydrophilicity. However, there is little control over individual droplet sizes and the timing of when those droplets impact the grid surface. Moreover, the liquid-handling devices used for these processes often entail large dead-volumes and thus specimen wastage, probably a primary reason why this particular method has not seen more mainstream usage.

The quality and thickness of the vitrified layer will depend on a number of factors including the properties of the specimen itself (e.g. viscosity, particle concentration), the nature of the substrate surface (e.g. hydrophobicity, flatness), the blotting paper (e.g. angle of contact, surface roughness, absorbency, blot time), and the plunging parameters (e.g. dwell time after blotting, speed of plunge, temperature of the cryogen). Thus, even highly skilled technicians may need to spend considerable effort optimizing this process for a new specimen; precious specimen is consumed by each trial, and time is required both in the laboratory and on the microscope to evaluate the prepared grids.

The present invention describes new technology for preparing thin films of vitrified sample using picoliter or nanoliter dispensing methodologies to dispense onto subregions of EM grids, depicted in FIG. 1B. This approach avoids the use of blotting paper and provides a very flat, highly controlled surface, thus considerably reducing many of the adverse factors that contribute to highly variable results with the current methods. The dispense system comprises of a dispense head that may be piezo-electric based, thermal or other inkjet technology related. The invention also describes a method to precisely control the time of sample dispense and EM grid plunge into liquid ethane, which is a critical component of the technology—to vitrify the sample before evaporation and drying can take place. Non-contact printing can be achieved using piezoelectric "inkjet" printing, a technology developed over the last 30 years. The technique involves utilizing a piezoelectric element to impulsively impart an acoustic pressure wave to liquid in the tip of a fine nozzle, causing a droplet of the liquid to be ejected from the tip. FIG. 1C. The voltage applied and the size of the nozzle determines the droplet volume, which can be precisely controlled to 10's of pL. Additionally, and of particular interest to cryo-TEM, is that piezo-electric based dispensing is compatible with a wide range of biological specimens such as nucleic acids, proteins, bacteria, mammalian cells, nanoparticles, micron-sized beads, polymers and aggregates.

The non-contact nature of the preferred dispensing system also provides complete independence from the substrate properties, opening up the possibility to tune surface properties and incorporate nano-structural features that can be precisely targeted. Droplet generation can be monitored in real-time and can be used as triggers for downstream instrumentation. Alternatively, the droplet generation itself can be triggered by upstream instrumentation, at time-scales of a few μsecs. The ability to position multiple dispense heads can allow for simultaneous multiple sample application onto a single substrate within a hundred micron separation. Inkjet dispensers can aspirate specimen volumes as low as 100 nL, dispense a precise volume (in discrete multiples of the droplet volume—10's of pL, and importantly retrieve any specimen remaining in the head. This feature is of particular interest when specimen availability is low (a situation for most eukaryotic complexes and membrane proteins). Moreover, inkjet print-heads are available commercially and are robust given the technological maturity of the microarray market. Given these technical and logistical advantages, we have initiated the integration of piezoelectric inkjet technology as a specimen application step in cryo-TEM to increase the efficiency of obtaining thin vitrified particles.

Figure 2:
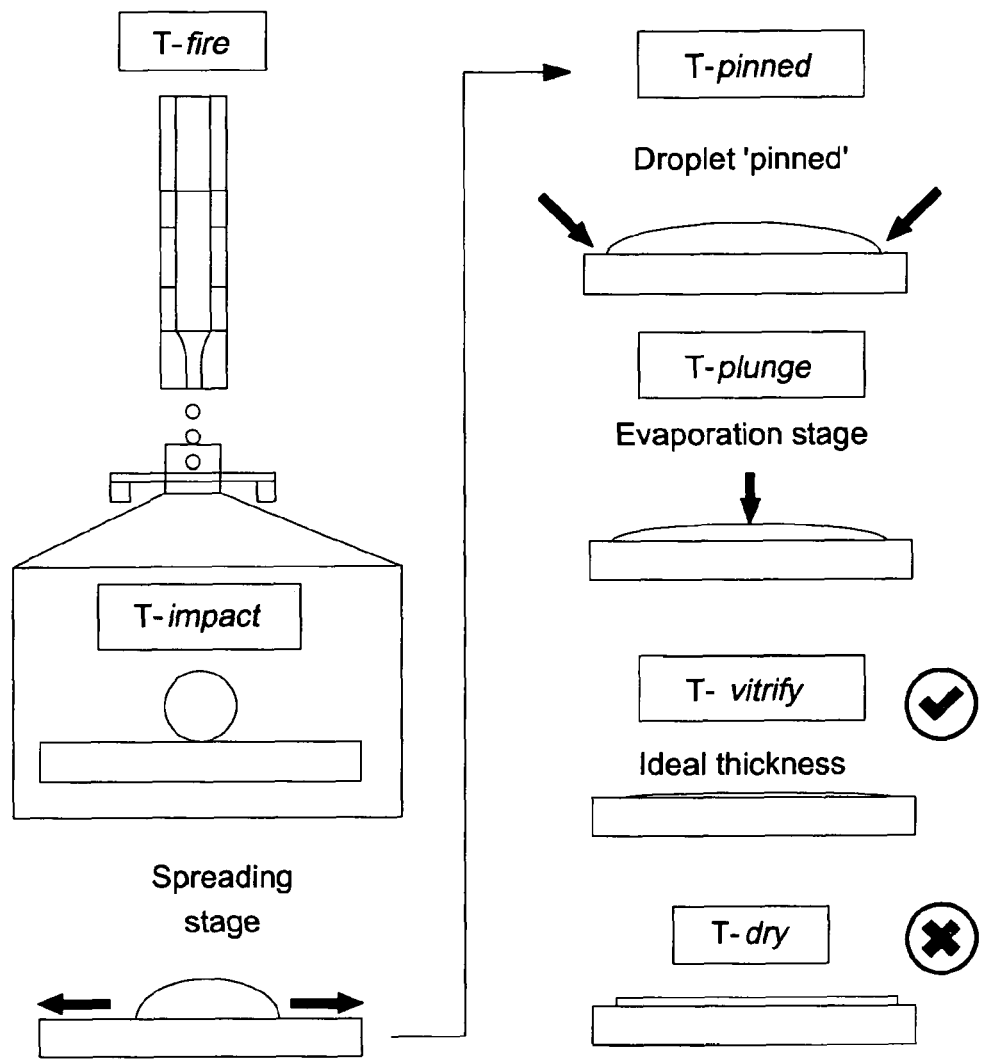

Important time-points starting from droplet launch out of the dispense head to the desired time of vitrification are indicated in FIG. 2. T-fire (zero) is the time the droplet leaves the dispense head. T-impact (on the order of a few msecs) is the time the droplet impacts the surface of the substrate, and T-pinned (order of tens of msecs) is the time to reach maximum contact diameter. Thereafter, the droplet is 'pinned' to the surface and is in evaporation phase. Tplunge (order of hundreds of msecs) is the time-point when the plunge trigger is generated and the sample reaches the liquid ethane at T-vitrify (order of hundreds of msecs). T-vitrify depends on the distance of the grid from the liquid ethane reservoir, the plunging mechanism (gravity, pneumatic or electronic drives), and plunge velocity. The vitrification phenomenon occurs within the microsecond timescale and is much faster relative to the other time periods mentioned here. The invention provides systems and methods that can more precisely control the (picoliter and nanoliter) dispense parameters (including volume, dispense velocity, head-grid separation) and the plunge mechanism. Light-weight high-speed motors and encoders (with speeds of several meters/second) are utilized to further enhance the positioning precision and speed of the plunging process.

Figure 3A:
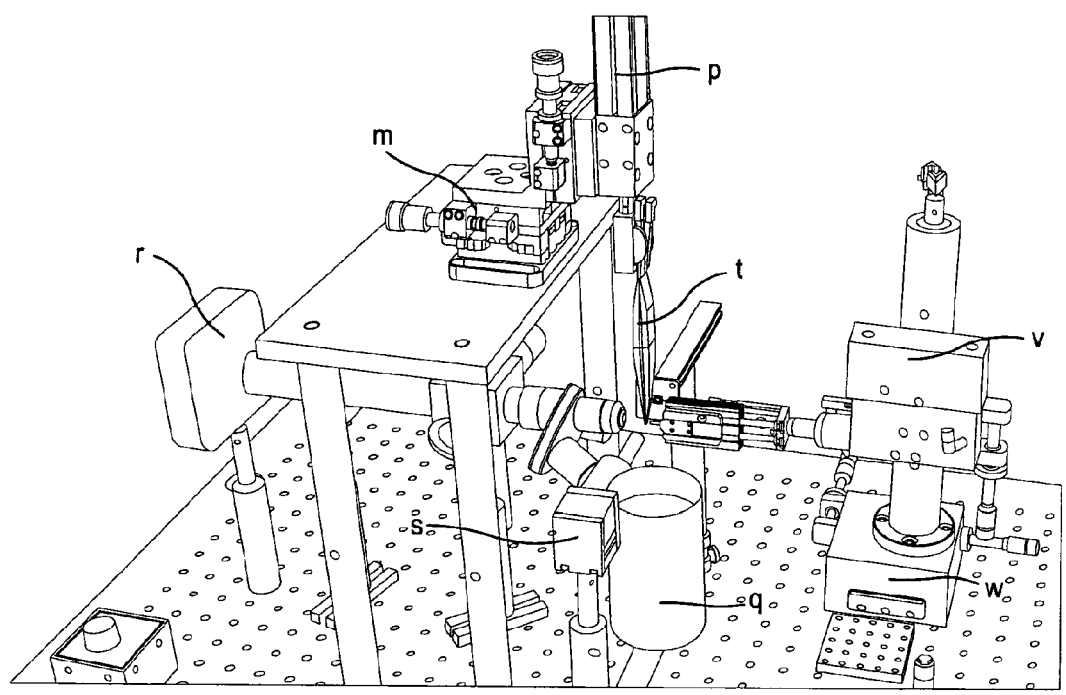
Figure 3B:
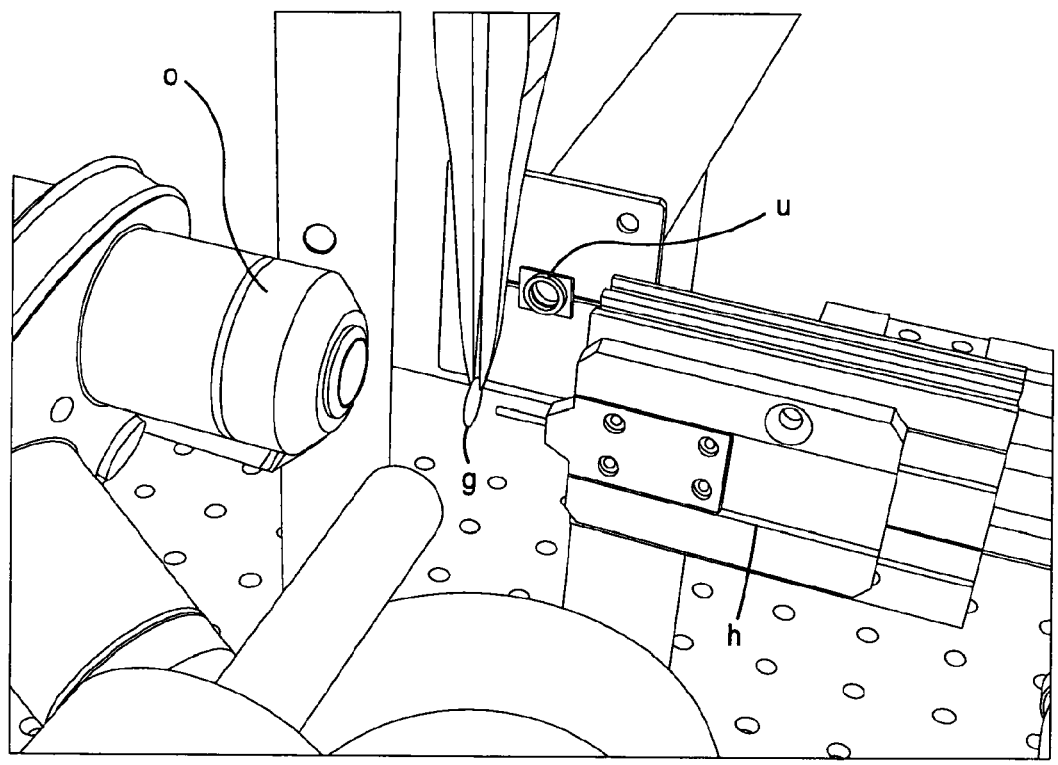

A basic schematic of the invention comprising of the dispense and vitrification system (dispense heads using inkjet technologies—thermal, bubble or piezoelectric) and other major components is shown in FIG. 3. An environmental chamber (not shown in figure) houses the entire setup to provide the desired ambient conditions of relative humidity and temperature. The plunge mechanism (p) comprises a motor drive, precisely controlled by a micron-precision linear encoder. The plunge assembly comprises the stem and a grid holder (t). While depicted in the figure as a pair of fine point tweezers, the grid holder is preferably precisely machined with clips to house the EM grid (g) and orient the confined areas horizontal and perpendicular to the system axis. This can act to prevent angular offset during droplet targeting.

An optional front looking camera (r) with optics (o) permitting a magnified view of the EM grid faces the plunge assembly and allows for confirming alignment of the droplets in relation to the mounted grid. Dispense heads (h), in this case piezo-electric heads designed for picoliter volumes, are stacked and the assembly mounted on an X-Y-Z stage (v) for positioning in relation to the plunge assembly. Each dispense head houses a linear direction set-screw, allowing for individual tuning of its position in relation to the stack (up to 2 mm). This ensures that each dispense head can access all locations of an EM grid, independent of the overall positioning of the stack assembly.

A side view camera (s) allows for head initialization and droplet monitoring using a LED strobe delay (u). This assembly is mounted on an X-Y-Z stage to ensure image focus in relation to all piezo-dispense heads. A removable sample reservoir (shown below w) is positioned vertically behind the plunge assembly and in direct path of the stack assembly. An electronic shutter controls the opening of the environment chamber for the plunge assembly to access the liquid ethane reservoir (q) at the final stage of the grids downwards trajectory. Both X-Y-Z stages can be either manually controlled or integrated with automatic drives. All electronics are controlled by a single computer interface and control code integrated in software and firmware.

Figure 4A:
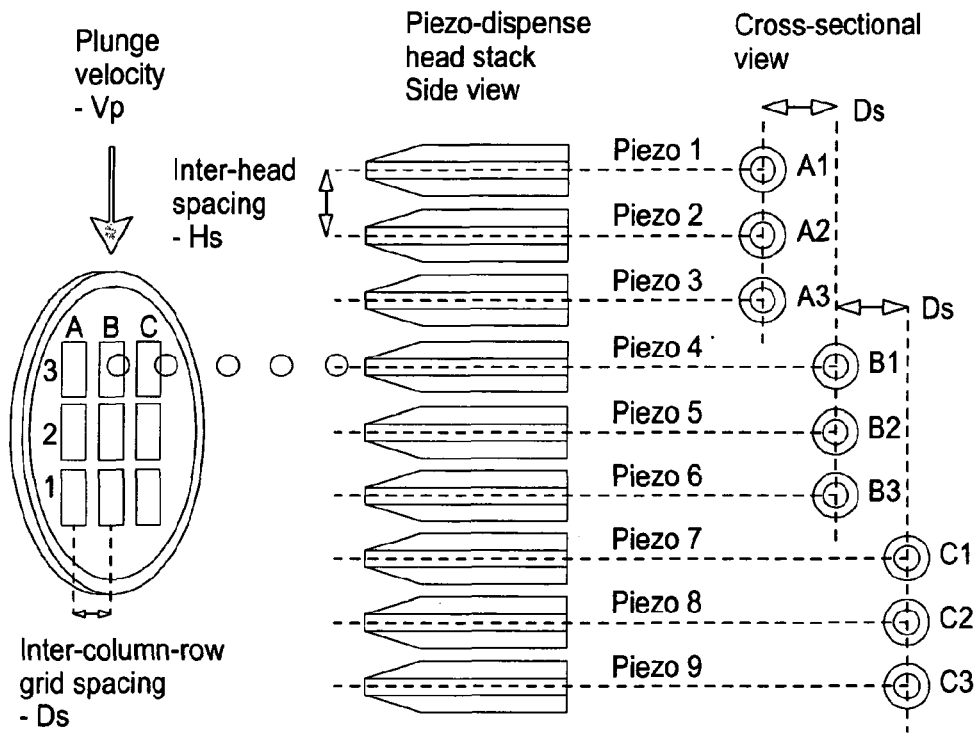
Figure 4A:
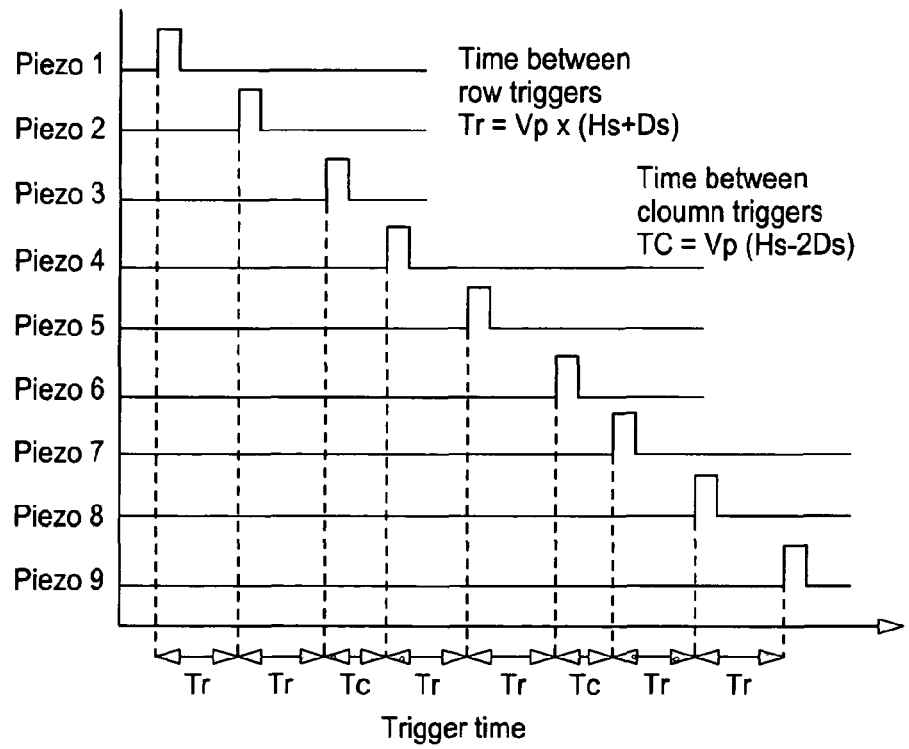
Figure 4B:
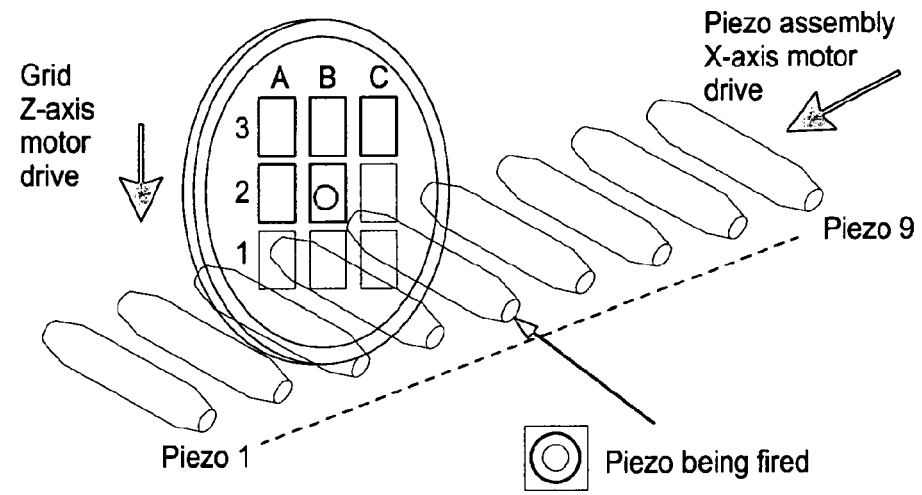
Figure 4B:
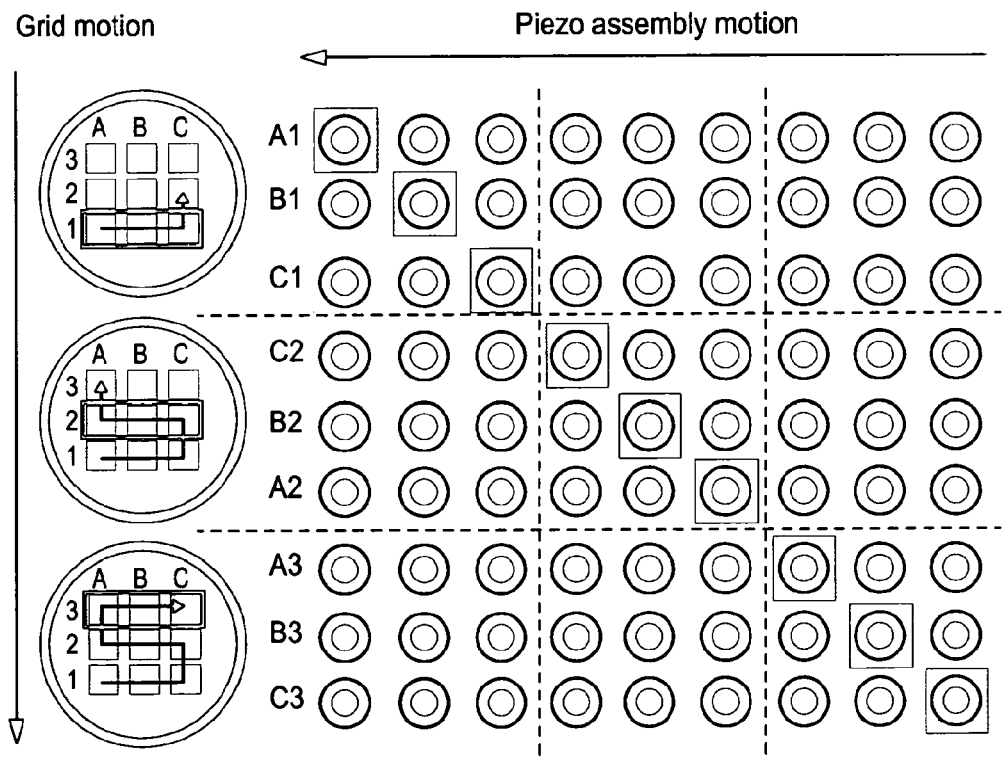

Two schemes for multiple-sample dispensing onto single EM grids are shown by which the invention achieves precision sub microliter dispense and spatial targeting. In the first scheme (FIG. 4A), the dispense head stack assembly is aligned and positioned with the grid. Individual dispense heads are staggered in space to target one of the three columns of a 3×3 array. During the dispense phase, the stack assembly position is maintained static, while the grid is driven downwards by the motor. Positional information provided by the precision linear encoder and dimension information of the design provides the exact trigger sequence of individual piezo-dispense heads. The trigger sequence of nine piezo-dispense heads depends on the velocity of the plunge assembly, the dimensions of the array layout on the grid and the inter-piezo-head spacing. In the second scheme (FIG. 4B), the piezo-head stack assembly is positioned vertically and its position driven perpendicular to the direction of the plunge assembly. In this scenario there is no need to spatially align individual piezo-dispense heads, but requires the use of automated position control during the dispense phase. Trigger sequence can be accurately timed by controlling both the grid and piezo-stack assembly position.

Figure 5:
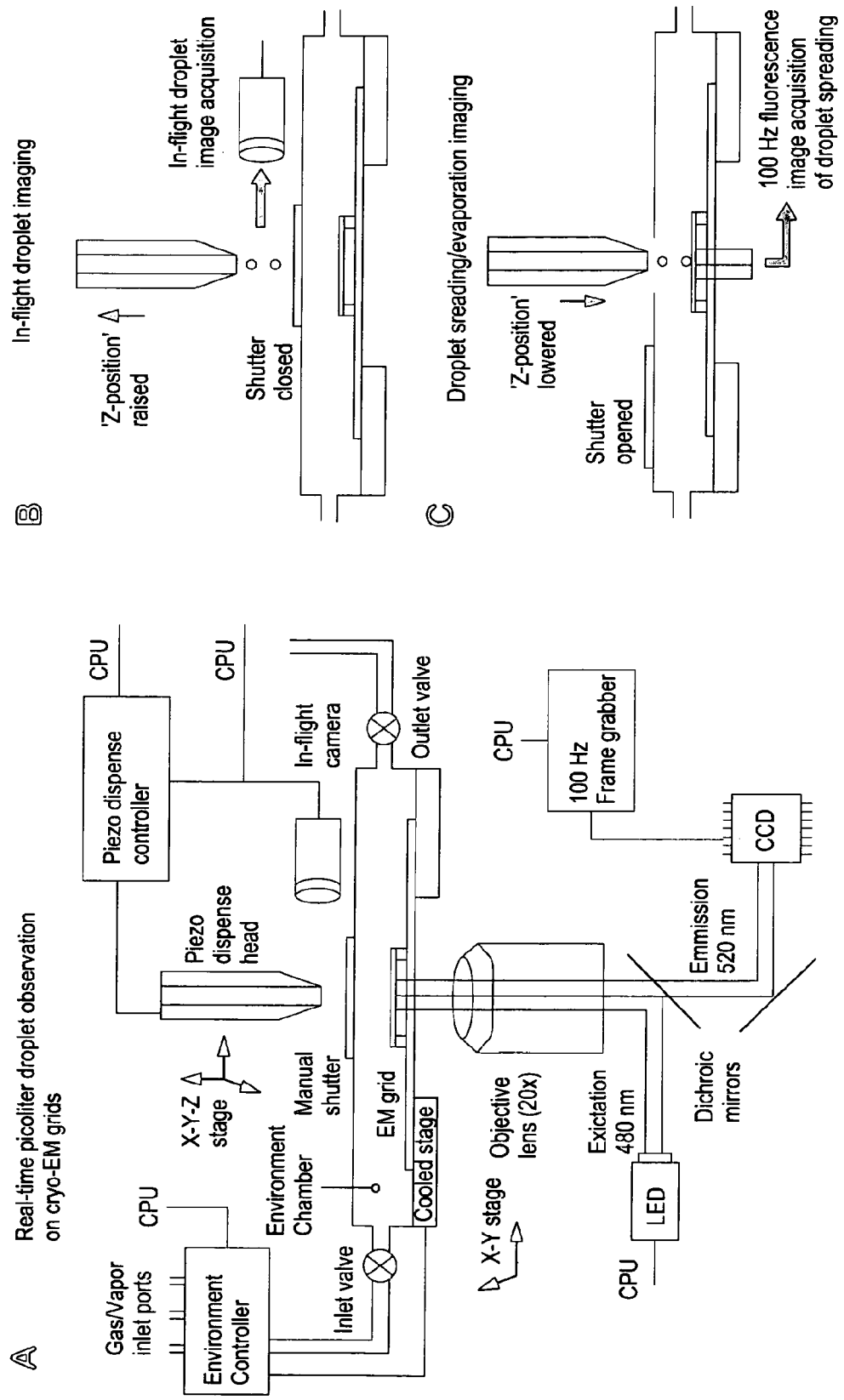

FIG. 5 depicts an exemplary embodiment of the system of the invention in schematic form. The system includes four major components: a piezo-dispense system, a high-speed fluorescence microscopy viewing system, an environmental control chamber and an in-flight droplet imager. The piezo-dispense comprises a drive electronics sub-system, one or more dispense heads with 24 µm diameter orifices, and the side camera visualization system that includes a CMOS USB camera, 5× lens and a controlled strobe light LED. The dispense head is capable of generating picoliter droplets of volume controlled by the drive electronics. The strobe and side visualization system is capable of high-speed inflight imaging of the fired droplets. The fluorescence system comprises a 20× objective lens, excitation/emission compatible optics with 488/520 nm filters will be custom configured to acquire 100 Hz frame rates using a CCD camera (DVC-340, DVC Inc.) that supports data transfer over a Gigabit Ethernet (GigE) interface. The environment chamber is custom designed with inlet and outlet ports controlled by a gas/vapor controlling unit (comprised cola humidifier and relative humidity sensors).

The top face of the chamber will include an access port with a mechanical shutter to position the piezo-dispense head over the EM grid. The chamber is positioned on a cooling stage (Bioscience tools, BTC-S) with a temperature controller (BTC-1-100) providing for a range of 0-100° C. at 0.1° C. resolution. The environment chamber/cooling stage assembly is positioned on an X-Y stage for positioning the EM grid relative to the objective lens. All control signals and acquisition data are synchronized in software.

A typical process flow will be comprised of: (1) place EM grid in chamber assembly and focus fluorescence scope; (2) stabilize chamber ambient conditions (temperature, humidity); (3) load the sample into the piezo-dispense head outside the chamber; (4) confirm in-flight droplet creation and integrity with top-port shutter closed; (5) open top port shutter and position piezo-dispense head at grid target area; (6) dispense picoliter volume onto the grid; (7) acquire fluorescent images at 100 Hz. Given that the grid area is 2 mm diameter and the spotting spread area (for picoliter volumes) is expected to be within 500 microns, multiple dispenses can be conducted on the same grid at different ambient and sample conditions by repeating the process.

EXAMPLES

Example 1

To test if picoliter to nanoliter dispensing of specimen using piezo-electric inkjet technology can be utilized for cryo-TEM, a system that integrated several modules as shown in FIG. 3. A commercially available piezo-electric dispense head was incorporated with central bore size 24 µm. This head was capable of dispensing discrete specimen droplets of 32 pL; observed in-flight using a stroboscopic LED light and side-view lens/camera system that allowed for viewing dispensed droplets at precise time-points (0-100 µsecs) after droplet generation from the head. Specimen dispense was triggered by software via the accompanying piezo-electric head control module and the number of droplets, frequency and droplet velocity could be modified as desired. Rear-view imaging of the grid at an acquisition rate of 100 Hz allowed for visualizing droplet impact, spreading and evaporation dynamics. The rear-view camera was also used to align the grid with the dispense head and provided a way to visualize different dispense conditions on the same grid (prior to vitrification). The grid and dispense head were independently manipulated for alignment using two 3-axis manual positioners, which allowed for precise targeting of specimen droplets on the grid. In order to retract the dispense head away immediately after dispense sequence was completed, the dispense head was mounted on a miniature pneumatic stage whose binary position (in or out) was controlled by a hand-operated pneumatic valve. A 90° rotation stage was incorporated to rotate the dispense head between the vertical (specimen aspiration) and horizontal (specimen dispense) positions, which also provided a way to retrieve remaining specimens in the dispense head. The vertical position allowed for specimens to be aspirated directly from vials and well-plates.

Example 2

Using the traditional sample pipetting and blotting technique the entire grid is affected, limiting only one specimen to be evaluated per grid during cryo-TEM study. The ability to precisely align and confine droplets on the substrate could open up the possibility to delivery multiple samples per grid, increasing the throughput of experimentation. Inkjet technology allows for precise positioning of dispense heads in relation to grid substrates, which provides a way to spatially control specimen dispensing on a single EM grid. Spatial targeting was confirmed by fluorescence imaging of the specimens (ex/em: 488/520 dye) on the grid. Droplet impact and spreading was further studied in hydrophobic and hydrophilic conditions. For untreated carbon grids the contact angle observed was ~90°, upon droplet dispensing (25 droplets) and image capture. In contrast, when the carbon grids were treated in an Oxygen/Argon plasma discharge, the contact angles reduced considerably to ~15°. This effect of surface wettability change was evaluated for small volume (64 pL, 2 droplets) targeted dispensing of fluorescent specimens on holey carbon grids by fluorescence and phase imaging. On hydrophobic grids the droplet spreading was non-uniform within the targeted squares, leading to aggregated areas. However, for hydrophilic grids the droplets spread out uniformly within the targeted squares and no aggregates were observed in both fluorescence and phase images.

Example 3

As one of the goals of this new methodology is to eliminate manual blotting, it is important that the samples on the grid be vitrified at time-points when the sample thickness is suitable for cryo-TEM imaging. This can be accomplished by viewing the droplet dynamics (spreading and drying) on the grid in real-time and triggering the plunge process (for vitrification) at an optimal time-point post-dispensing. At the experimental environment conditions (RH 10%, Temperature 25° C.), a single droplet dries (as observable by rear-view imaging) within 300 msec upon impact onto the grid. Under these conditions, higher number of droplets led to longer drying times (and also larger spreading distances on the grid; data not shown). Also, the repeatability of the droplet dynamics (based on drying times) is high for the droplets dispensed on the grid, allowing for automated plunging events to be accurately timed. In the current system, the plunging event is triggered manually by a hand-operated pneumatic valve, under visual feedback from the real-time camera. Operator reaction times were not accurate within the 100 msec-1 sec range. Therefore, for the purpose of experimentation, larger droplet numbers (>50), giving longer times to asses droplet spreading and drying effects, were used to vitrify samples.

Example 4

Inkjet dispensing has been successfully used in developing protein and antibody arrays for a variety of applications. Given the functional preservation of protein and antibodies after dispensing in these applications, it can be assumed that the dispensing method itself does not greatly compromise the stability of the biological macromolecules. However, in all the previous applications, the assay readouts (mostly fluorescence or colorimetric) were not molecular imaging based, and therefore it could not be concluded with certainty what population of dispensed macromolecules were structurally preserved. For application of inkjet technology to TEM imaging, it is imperative that the dispensing technology itself does not degrade the macromolecules or their complexes; else imaging results will lead to artifacts and broken particles. Therefore, to evaluate the effect of the piezo-electric inkjet heads on particle structure stability, several macromolecules with known structures (GroEL, Microtubules, Lipid Nanotubes, Cucumber Necrosis Virus) were dispensed (32 nL, 1000 droplets) onto carbon-film grids and then subsequently negative stained manually with 2% Uranyl Acetate (performed within 10 secs of dispensing). Particles in all four cases were structurally intact (comparable to their previously known structures) with no evidence of any instability. To further assess the compatibility of piezo-electric inkjet dispensing for maintaining functional activity of eukaryotic complexes, human Dicer/TRBP complex was dispensed via the piezo-electric inkjet head into a test aliquot and its ability to dice double stranded RNA compared to control aliquots. Results indicated that the inkjet dispensing did not affect the dicing activity of the Dicer/TRBP complex as assessed by an RNA gel.

The next step was to confirm the ability of the integrated inkjet dispensing, plunging and vitrification system to obtain samples suitable for cryo-TEM imaging. For this purpose, 1.6 nL (50 droplets) of Tobacco Mosaic Virus (TMV) and 3.2 nl (100 droplets) of a molecular chaperone (GroEL), were dispensed onto continuous carbon and holey carbon grids, respectively, and vitrified at time-points prior to complete drying. All experimental conditions were at RH 10% and temperature 25° C., with the plunge process triggered under manual operator control (using real-time visual feedback from the rear-view camera). The continuous carbon grids provided a non-porous surface for droplet spreading, which allowed for uniform spreading in a radial manner. Also, after the spreading was complete (within 200 msec) and the droplet was pinned, drying patterns could be observed within 2 secs. On visual onset of the drying patterns, the grids were plunged for vitrification and imaged using cryo-TEM.

At low magnification, typical spot profiles were circular with dark (thicker) center areas and lighter (thinner) areas toward the perimeter. Specimen vitrification was thin enough to visualize TMV particles at high-magnification in the peripheral areas. In the case of holey carbon grids (porous due to the 2 μm holes), the spreading profile was more complex. Instead of uniform circular spreading, the dispensed volume traversed through the 2 μm holes in the carbon membrane to both sides of the grid, contacting the support copper mesh, which induced local droplet dynamics within the squares. Sample spreading over the grid is complete within 300 msec and the manual plunge triggered at 4 secs, when the sample was observed receding due to evaporation. Low-magnification cryo-TEM images indicated individual squares displaying local droplet drying dynamics. Squares on the grid could be identified where vitrified sample was thin enough for visualizing GroEL over the holes at high-magnification. For TMV particles, the 23 A° diffraction patterns were identifiable, and for GroEL, two-dimensional class averages of picked particles indicated seven-fold symmetry—both results suggesting preservation of particle structure.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations that is not specifically disclosed herein. Thus, for example, in each instance herein any of the terms "comprising," "consisting essentially of" and "consisting of" may be replaced with either of the other two terms. The terms and expressions that have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A system for preparing an electron microscopy sample on an EM sample grid, comprising:
   a. a plunger assembly comprising a shaft operably connected to a shaft drive assembly, a triggering mechanism, and a holder for reversibly receiving an EM sample grid at a first end of the shaft, the shaft drive assembly and triggering mechanism configured to (i) position the EM sample grid at a first position prior to a trigger event, and (ii) displace the shaft in a first direction at a predetermined rate and position the EM sample grid at a second position following a trigger event;
   b. a fluid dispenser configured to dispense fluid from one or more dispensing elements onto one or more independently addressable subregions of the EM sample grid in the first position or between the first and second positions, wherein the one or more dispensing elements dispense a picoliter sample volume by thermal inkjet printing, acoustic inkjet printing, or piezoelectric inkjet printing onto the one or more independently addressable subregions of the EM sample grid, or wherein the one or more dispensing elements comprise one or more print pins that dispense a picoliter sample volume by physical contact with one or more subregions of the EM sample grid;
   c. a sample reservoir operably linked to the fluid dispenser; and
   d. a cryogen reservoir configured to position a cryogenic liquid at the second position.

2. A system according to claim 1, wherein the one or more dispensing elements dispense a picoliter sample volume by thermal inkjet printing, acoustic inkjet printing, or piezoelectric inkjet printing onto the one or more independently addressable subregions of the EM sample grid.

3. A system according to claim 1, wherein the one or more dispensing elements comprise one or more print pins that dispense a picoliter sample volume by physical contact with one or more subregions of the EM sample grid.

4. A system according to claim 1, wherein the fluid dispenser is operably connected to a positioning drive configured to provide adjustment of the drop dispenser relative to the EM sample grid in the first position or between the first and second positions.

5. A system according to claim 1, wherein the fluid dispenser comprises a plurality of dispensing elements configured to dispense a picoliter sample volume onto different independently addressable subregions of the EM sample grid.

6. A system according to claim 1, further comprising an environmental chamber configured to provide controlled relative humidity and temperature.

7. A system according to claim 1, further comprising one or both of (i) and (ii):
   (i) a first camera system configured to provide monitoring of fluid dispensed from the one or more dispensing elements, and
   (ii) a second camera system configured to provide monitoring alignment of the position of the dispensing elements relative to the EM sample grid in the first position and/or monitoring of droplet characteristics on the EM sample grid.

8. A system according to claim 1, wherein the shaft drive assembly comprises a pneumatic drive.

9. A system according to claim 1, wherein the shaft drive assembly comprises a stepper motor drive.

10. A system according to claim 1, comprising a computer interface configured to control operation of one or more system elements.

11. A method for preparing an electron microscopy sample on an EM sample grid, comprising:
    a. positioning the EM sample grid on a plunger assembly, the plunger assembly comprising a shaft operably connected to a shaft drive assembly, a triggering mechanism, and a holder for reversibly receiving the EM sample grid at a first end of the shaft, the shaft drive assembly and triggering mechanism configured to (i) position the EM sample grid at a first position prior to a trigger event, and (ii) displace the shaft in a first direction at a predetermined rate and position the EM sample grid at a second position following a trigger event;
    b. with the EM sample grid in the first position or between the first and second positions, dispensing one or more sample volumes onto one or more independently addressable subregions of the EM sample grid using a fluid dispenser configured to dispense fluid from one or more dispensing elements, wherein the one or more dispensing elements dispense a picoliter sample volume by thermal inkjet printing, acoustic inkjet printing, or piezoelectric inkjet printing onto the one or more independently addressable subregions of the EM sample grid, or wherein the one or more dispensing elements comprise one or more print pins that dispense a picoliter sample volume by physical contact with one or more subregions of the EM sample grid;
    c. activating the triggering mechanism to displace the shaft to the second position, wherein the EM sample grid is immersed into a cryogenic liquid contained within a cryogen reservoir.

12. A method according to claim 11, wherein the one or more dispensing elements dispense a picoliter sample volume by thermal inkjet printing, acoustic inkjet printing, or piezoelectric inkjet printing onto the one or more independently addressable subregions of the EM sample grid.

13. A method according to claim 11, wherein the one or more dispensing elements comprise one or more print pins that dispense a picoliter sample volume by physical contact with one or more subregions of the EM sample grid.

14. A method according to claim 11, wherein the fluid dispenser is operably connected to a positioning drive configured to provide adjustment of the drop dispenser relative to the EM sample grid.

15. A method according to claim 11, wherein the fluid dispenser comprises a plurality of dispensing elements that dispense a picoliter sample volume onto different independently addressable subregions of the EM sample grid.

16. A method according to claim 11, further comprising maintaining the EM sample grid in a controlled relative humidity and temperature environment during at least step (b).

17. A method according to claim 11, further comprising one or both of (i) and (ii):
   (i) monitoring of fluid dispensed from the one or more dispensing elements using a first camera system, and
   (ii) monitoring alignment of the position of the dispensing elements relative to the EM sample grid in the first position and/or monitoring of droplet characteristics on the EM sample grid using a second camera system.

18. A method according to claim 11, wherein the shaft drive assembly comprises a pneumatic drive.

19. A method according to claim 11, wherein the shaft drive assembly comprises a stepper motor drive.

* * * * *